(12) United States Patent
Paraschac et al.

(10) Patent No.: US 9,241,706 B2
(45) Date of Patent: *Jan. 26, 2016

(54) SUTURE LOCKING DEVICE AND METHODS

(75) Inventors: Joseph Francis Paraschac, San Jose, CA (US); Scott A. McIntosh, Sunnyvale, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 353 days.

This patent is subject to a terminal disclaimer.

(21) Appl. No.: 13/356,129

(22) Filed: Jan. 23, 2012

(65) Prior Publication Data

US 2012/0184991 A1    Jul. 19, 2012

Related U.S. Application Data

(63) Continuation of application No. 10/941,693, filed on Sep. 15, 2004, now Pat. No. 8,100,923.

(60) Provisional application No. 60/502,925, filed on Sep. 15, 2003.

(51) Int. Cl.
*A61B 17/04* (2006.01)
*A61B 17/12* (2006.01)
*A61B 17/00* (2006.01)

(52) U.S. Cl.
CPC ......... *A61B 17/0467* (2013.01); *A61B 17/0487* (2013.01); *A61B 17/12009* (2013.01); *A61B 17/12013* (2013.01); *A61B 2017/00243* (2013.01); *A61B 2017/045* (2013.01);
(Continued)

(58) Field of Classification Search
CPC ........... A61B 17/0401; A61B 17/0487; A61B 2017/0409; A61B 2017/0414; A61B 2017/0488; A61B 17/0467; A61B 2017/045; A61B 2017/0451

USPC ................ 606/139, 144–148, 232; 24/115 R, 24/114.5, 130
See application file for complete search history.

(56) References Cited

U.S. PATENT DOCUMENTS

| | | | |
|---|---|---|---|
| 2,238,563 | A | 4/1941 | Jacques |
| 2,416,260 | A | 2/1947 | Karle |

(Continued)

FOREIGN PATENT DOCUMENTS

| | | |
|---|---|---|
| WO | WO 02/15795 | 2/2002 |
| WO | WO 2005/027754 | 3/2005 |

OTHER PUBLICATIONS

U.S. Appl. No. 13/022,246, Jun. 7, 2013, Office Action.
(Continued)

*Primary Examiner* — Kathleen Holwerda
(74) *Attorney, Agent, or Firm* — Workman Nydegger; Randy Shen (57) ABSTRACT

Devices and methods for securing a pair of suture lengths together or for using a single strand of suture to secure tissue (s) together at an operative site in a patient without necessarily tying a knot. The suture lock device includes a suturing securing device having an outer body member having a lumen extending therethrough. The lumen defines a suture path through the outer body. An inner wedge member is axially insertable into the outer body member to secure a portion of a suture between the wedge and the interior surface of the lock member. An outer tube has a proximal end and a distal end. The outer tube carries the outer body member at the distal end of the outer tube. The outer tube carries the wedge proximal to the outer body member.

16 Claims, 11 Drawing Sheets

(52) U.S. Cl.
CPC . *A61B2017/0445* (2013.01); *A61B 2017/0448* (2013.01); *A61B 2017/0488* (2013.01); *A61B 2017/0496* (2013.01)

(56) References Cited

U.S. PATENT DOCUMENTS

| | | | |
|---|---|---|---|
| 2,449,235 A | | 9/1948 | Krupp |
| 3,766,610 A | * | 10/1973 | Thorsbakken ............... 403/211 |
| 3,877,434 A | | 4/1975 | Ferguson et al. |
| 4,156,574 A | | 5/1979 | Boden |
| 4,705,040 A | | 11/1987 | Mueller et al. |
| 4,750,492 A | | 6/1988 | Jacobs |
| 4,807,333 A | | 2/1989 | Boden |
| 5,292,332 A | | 3/1994 | Lee |
| 5,342,393 A | | 8/1994 | Stack |
| 5,364,408 A | | 11/1994 | Gordon |
| 5,383,905 A | | 1/1995 | Golds et al. |
| 5,391,200 A | | 2/1995 | KenKnight et al. |
| 5,417,699 A | | 5/1995 | Klein et al. |
| 5,435,044 A | | 7/1995 | Ida |
| 5,454,140 A | | 10/1995 | Murai |
| 5,462,558 A | | 10/1995 | Kolesa et al. |
| 5,478,353 A | | 12/1995 | Yoon |
| 5,501,692 A | | 3/1996 | Riza |
| 5,507,754 A | | 4/1996 | Green et al. |
| 5,520,070 A | | 5/1996 | Beugelsdyk et al. |
| 5,520,702 A | * | 5/1996 | Sauer et al. ............... 606/144 |
| 5,562,688 A | | 10/1996 | Riza |
| 5,562,689 A | | 10/1996 | Green et al. |
| 5,569,306 A | | 10/1996 | Thal |
| 5,572,770 A | | 11/1996 | Boden |
| 5,575,800 A | | 11/1996 | Gordon |
| 5,584,861 A | | 12/1996 | Swain et al. |
| 5,613,974 A | | 3/1997 | Andreas et al. |
| 5,630,824 A | * | 5/1997 | Hart ............... 606/139 |
| 5,645,553 A | | 7/1997 | Kolesa et al. |
| 5,658,313 A | | 8/1997 | Thal |
| 5,662,664 A | | 9/1997 | Gordon et al. |
| 5,700,272 A | | 12/1997 | Gordon et al. |
| 5,702,397 A | | 12/1997 | Goble et al. |
| 5,725,529 A | | 3/1998 | Nicholson et al. |
| 5,779,707 A | | 7/1998 | Bertholet et al. |
| 5,868,762 A | | 2/1999 | Cragg et al. |
| 5,893,856 A | | 4/1999 | Jacob et al. |
| 5,899,921 A | * | 5/1999 | Caspari et al. ............... 606/232 |
| 5,902,311 A | | 5/1999 | Andreas et al. |
| 5,941,901 A | | 8/1999 | Egan |
| 6,066,160 A | | 5/2000 | Colvin et al. |
| 6,086,608 A | * | 7/2000 | Ek et al. ............... 606/232 |
| 6,099,547 A | | 8/2000 | Gellman et al. |
| 6,136,010 A | | 10/2000 | Modesitt et al. |
| 6,190,414 B1 | | 2/2001 | Young et al. |
| 6,200,329 B1 | | 3/2001 | Fung et al. |
| 6,203,554 B1 | | 3/2001 | Roberts |
| 6,206,895 B1 | | 3/2001 | Levinson |
| 6,228,096 B1 | | 5/2001 | Marchand |
| 6,231,592 B1 | | 5/2001 | Bonutti et al. |
| 6,245,080 B1 | | 6/2001 | Levinson |
| 6,277,140 B2 | | 8/2001 | Ginn et al. |
| 6,398,796 B2 | | 6/2002 | Levinson |
| 6,475,230 B1 | * | 11/2002 | Bonutti et al. ............... 606/232 |
| 6,712,837 B2 | | 3/2004 | Akerfeldt et al. |
| 6,746,457 B2 | | 6/2004 | Dana et al. |
| 6,786,915 B2 | | 9/2004 | Akerfeldt et al. |
| 7,011,400 B2 | | 3/2006 | Nakano |
| 7,033,370 B2 | | 4/2006 | Gordon et al. |
| 7,060,077 B2 | | 6/2006 | Gordon et al. |
| 7,147,646 B2 | | 12/2006 | Dana et al. |
| 7,320,693 B2 | | 1/2008 | Pollack et al. |
| 7,361,183 B2 | | 4/2008 | Ginn |
| 7,390,328 B2 | | 6/2008 | Modesitt |
| 7,435,251 B2 | | 10/2008 | Green |
| 7,662,161 B2 | | 2/2010 | Briganti et al. |
| 7,713,284 B2 | | 5/2010 | Crofford |
| 7,842,051 B2 | | 11/2010 | Dana et al. |
| 7,875,043 B1 | | 1/2011 | Ashby et al. |
| 7,931,670 B2 | | 4/2011 | Fiehler et al. |
| 7,947,062 B2 | | 5/2011 | Chin et al. |
| 8,048,108 B2 | | 11/2011 | Sibbitt, Jr. et al. |
| 8,100,923 B2 | | 1/2012 | Paraschac et al. |
| 8,128,652 B2 | | 3/2012 | Paprocki |
| 8,128,653 B2 | | 3/2012 | McGuckin, Jr. et al. |
| 8,262,736 B2 | | 9/2012 | Michelson |
| 8,337,522 B2 | | 12/2012 | Ditter |
| 8,480,691 B2 | | 7/2013 | Dana et al. |
| 8,579,934 B2 | | 11/2013 | Ginn |
| 8,647,364 B2 | | 2/2014 | Fiehler et al. |
| 8,932,324 B2 | | 1/2015 | Sibbitt, Jr. et al. |
| 8,932,327 B2 | | 1/2015 | Kosa et al. |
| 8,945,180 B2 | | 2/2015 | Roorda |
| 2001/0023352 A1 | | 9/2001 | Gordon et al. |
| 2001/0044638 A1 | | 11/2001 | Levinson et al. |
| 2001/0044639 A1 | | 11/2001 | Levinson |
| 2002/0002401 A1 | | 1/2002 | McGuckin, Jr. et al. |
| 2002/0077658 A1 | | 6/2002 | Ginn |
| 2002/0082641 A1 | | 6/2002 | Ginn et al. |
| 2002/0107542 A1 | | 8/2002 | Kanner et al. |
| 2002/0151921 A1 | | 10/2002 | Kanner et al. |
| 2002/0169478 A1 | | 11/2002 | Schwartz et al. |
| 2002/0188318 A1 | | 12/2002 | Carley et al. |
| 2003/0093096 A1 | | 5/2003 | McGuckin, Jr. et al. |
| 2003/0144695 A1 | | 7/2003 | McGuckin, Jr. et al. |
| 2003/0167062 A1 | | 9/2003 | Gamabale et al. |
| 2003/0195514 A1 | | 10/2003 | Trieu et al. |
| 2003/0199987 A1 | | 10/2003 | Berg et al. |
| 2004/0093024 A1 | | 5/2004 | Lousararian et al. |
| 2004/0122451 A1 | | 6/2004 | Wood |
| 2004/0158309 A1 | | 8/2004 | Wachter et al. |
| 2005/0038500 A1 | | 2/2005 | Boylan et al. |
| 2005/0085853 A1 | | 4/2005 | Forsberg et al. |
| 2005/0096697 A1 | | 5/2005 | Forsberg et al. |
| 2005/0205640 A1 | | 9/2005 | Milliman |
| 2006/0190037 A1 | | 8/2006 | Ginn et al. |
| 2006/0235505 A1 | | 10/2006 | Oepen et al. |
| 2006/0241579 A1 | | 10/2006 | Kawaura et al. |
| 2006/0265008 A1 | | 11/2006 | Maruyama et al. |
| 2006/0265010 A1 | | 11/2006 | Paraschac et al. |
| 2007/0010853 A1 | | 1/2007 | Ginn et al. |
| 2007/0060895 A1 | | 3/2007 | Sibbitt, et al. |
| 2007/0149987 A1 | | 6/2007 | Wellman et al. |
| 2007/0255317 A1 | | 11/2007 | Fanton et al. |
| 2007/0260125 A1 | | 11/2007 | Strauss et al. |
| 2007/0270904 A1 | | 11/2007 | Ginn |
| 2007/0276433 A1 | | 11/2007 | Huss |
| 2007/0276488 A1 | | 11/2007 | Wachter et al. |
| 2008/0065156 A1 | | 3/2008 | Hauser et al. |
| 2008/0114395 A1 | | 5/2008 | Mathisen et al. |
| 2008/0312740 A1 | | 12/2008 | Wachter et al. |
| 2009/0012537 A1 | | 1/2009 | Green |
| 2009/0069847 A1 | | 3/2009 | Hashiba et al. |
| 2009/0157102 A1 | | 6/2009 | Reynolds et al. |
| 2009/0306671 A1 | | 12/2009 | McCormack et al. |
| 2009/0306685 A1 | | 12/2009 | Fill |
| 2010/0042144 A1 | | 2/2010 | Bennett |
| 2010/0179589 A1 | | 7/2010 | Roorda et al. |
| 2010/0179590 A1 | | 7/2010 | Fortson et al. |
| 2010/0256670 A1 | | 10/2010 | Ginn et al. |
| 2011/0029012 A1 | | 2/2011 | Tegels |
| 2012/0109189 A1 | | 5/2012 | Voss et al. |
| 2012/0203328 A1 | | 8/2012 | Yribarren |
| 2012/0220833 A1 | | 8/2012 | Ehrenreich |
| 2013/0046331 A1 | | 2/2013 | Christensen et al. |
| 2013/0053884 A1 | | 2/2013 | Roorda |
| 2013/0103077 A1 | | 4/2013 | Ditter |
| 2013/0110165 A1 | | 5/2013 | Burkhart et al. |
| 2013/0218206 A1 | | 8/2013 | Gadlage |
| 2013/0296887 A1 | | 11/2013 | Dana et al. |
| 2013/0345745 A1 | | 12/2013 | Kim |
| 2014/0039271 A1 | | 2/2014 | Ehrenreich |
| 2014/0148824 A1 | | 5/2014 | Fujisaki et al. |
| 2014/0228868 A1 | | 8/2014 | Hassan et al. |
| 2014/0336702 A1 | | 11/2014 | Rowe et al. |
| 2014/0364904 A1 | | 12/2014 | Kim |

OTHER PUBLICATIONS (56) References Cited

OTHER PUBLICATIONS

U.S. Appl. No. 12/917,195, Aug. 7, 2013, Notice of Allowance.
U.S. Appl. No. 13/219,004, Aug. 9, 2013, Office Action.
U.S. Appl. No. 13,411,320, filed Mar. 2, 2012, Voss et al.
U.S. Appl. No. 12/684,470, filed Jan. 8, 2010, Voss et al.
U.S. Appl. No. 12/917,195, Jun. 28, 2012, Office Action.
U.S. Appl. No. 12/917,195, Aug. 1, 2012, Office Action.
U.S. Appl. No. 13/022,246, May 11, 2012, Office Action.
U.S. Appl. No. 13/022,246, Nov. 28, 2012, Office Action.
U.S. Appl. No. 13/035,939, Jan. 31, 2013, Office Action.
U.S. Appl. No. 13/219,004, Dec. 19, 2012, Office Action.
U.S. Appl. No. 13/219,004, Feb. 14, 2013, Office Action.
U.S. Appl. No. 60/502,925, filed Sep. 15, 2003, Paraschac.
U.S. Appl. No. 10/941,693, Nov. 17, 2006, Office Action.
U.S. Appl. No. 10/941,693, May 7, 2007, Office Action.
U.S. Appl. No. 10/941,693, Dec. 31, 2007, Office Action.
U.S. Appl. No. 10/941,693, Jul. 9, 2008, Office Action.
U.S. Appl. No. 10/941,693, Mar. 2, 2009, Office Action.
U.S. Appl. No. 10/941,693, Oct. 23, 2009, Office Action.
U.S. Appl. No. 10/941,693, Sep. 28, 2011, Notice of Allowance.
U.S. Appl. No. 11/460,863, Jul. 12, 2007, Office Action.
U.S. Appl. No. 11/460,863, Feb. 5, 2008, Office Action.
U.S. Appl. No. 11/460,863, Oct. 10, 2008, Office Action.
U.S. Appl. No. 11/460,863, Apr. 13, 2009, Office Action.
U.S. Appl. No. 12/917,195, May 6, 2013, Office Action.
U.S. Appl. No. 13/022,246, Nov. 14, 2013, Notice of Allowance.
U.S. Appl. No. 13/035,939, Sep. 10, 2013, Office Action.
U.S. Appl. No. 13/035,939, Apr. 10, 2014, Office Action.
U.S. Appl. No. 13/219,004, Aug. 5, 2014, Office Action.
U.S. Appl. No. 13/035,939, Aug. 21, 2014, Office Action.
U.S. Appl. No. 14/052,658, Sep. 4, 2014, Office Action.
U.S. Appl. No. 13/411,320, Feb. 3, 2015, Office Action.
U.S. Appl. No. 13/219,004, Feb. 17, 2015, Notice of Allowance.
U.S. Appl. No. 13/035,939, Mar. 13, 2015, Office Action.
U.S. Appl. No. 13/411,320, May 27, 2015, Notice of Allowance.
U.S. Appl. No. 13/219,004, May 27, 2015, Issue Notification.
U.S. Appl. No. 14/052,658, Mar. 27, 2015, Office Action.

* cited by examiner

SUTURE LOCKING DEVICE AND METHODS

PRIORITY CLAIM

This application is a continuation of U.S. application Ser. No. 10/941,693, filed Sep. 15, 2004, now U.S. Pat. No. 8,100,923, which claims the benefit of U.S. Provisional Patent Application Ser. No. 60/502,925, filed Sep. 15, 2003, the entireties which are hereby incorporation by reference.

FIELD OF THE INVENTION

The present invention relates to devices and methods for securing a pair of suture lengths together or for using a single strand of suture to secure tissue(s) together at an operative site in a patient without necessarily tying a knot.

BACKGROUND

Sutures are used to sew tissue together, and thereby close tissue openings, cuts or incisions during or after any of a very wide variety of medical procedures. Additionally sutures may be utilized to correct patent foramen ovales (PFO) which are openings between the two atria of the heart. Typically, the surgeon manually ties together a suture pair to close the opening. A variety of automatic suture tying systems and suture securing mechanisms have been developed.

Manually tying sutures together to secure tissue can be very difficult and challenging. For example, manual knot tying requires considerable dexterity in the context of a medical procedure where the surgeon's hands are gloved or when the suturing is being performed in a part of a patient's anatomy that is particularly difficult to access. Also, in minimally invasive surgical procedures or in the case of closure of a puncture in a femoral artery after a catheterization procedure, the space adjacent the wound or tissue opening to be sutured is limited by other parts of the patient's anatomy and in many instances the opening to be closed cannot be visualized, therefore the knot must be formed blindly.

Also, manual knot tying can be time consuming as well as difficult in instances where the tying process cannot be visualized. Knot tying is further complicated by the fact that surgical sutures generally have low friction surfaces. Therefore, it is typically necessary for a surgeon to include many loops or "throws" when tying a knot. Multiple throws are often required even if an automatic knot tying device is used such as that disclosed in U.S. Pat. No. 6,171,317 the entirety of which is hereby incorporated by reference. Unfortunately, as the number of loops or "throws" incorporated into the knot increases, the knot becomes increasingly large and bulky. Manually tied knots also can become "locked" prior to reaching the intended amount of tension to be applied to the tissue. If the knot becomes "locked" prior to final deployment, the surgeon may be required to remove the suture and place a new suture if possible or resort to other closure methods such as compression if the suture was being utilized to close an opening in a vessel.

Moreover, the surgeon typically needs to handle suture strands having adequate length prior to commencing manual knot tying. Thus, manual knot tying requires considerable space both in which to view, and to perform, the actual knot tying. Therefore, knot tying is particularly difficult in areas of limited available space or access, for example, at the back of the patient's heart during a coronary artery bypass graft (CABG) operation or in a tissue tract resulting from a percutaneous transluminal catheterization procedure.

In addition to those problems described above, many of the sutures utilized for surgical procedures can only be manipulated to a certain degree before failure. For example, when tightening a knot, the suture is placed in tension by the surgeon, too much tension applied to the suture may cause the suture to break. Alternatively, too much tension applied to the suture may cause the suture to be torn from the tissue further complicating closure by creating a larger wound or opening in the tissue which then must be addressed.

Many knot replacement technologies for use with sutures have been proposed over the years, one example of a knot replacement technology is a deformable clip. Wherein the suture ends are disposed through a deformable member which is then deformed thereby trapping the suture therein. A shortcoming of this design is that the deformable member must be made to be sufficiently deformable but yet have enough strength to retain the suture therein. Further still, there is the possibility of the suture slipping from the deformed clip if the clip was not deformed sufficiently. Lastly, many of these deformable clips are constructed of non-absorbable materials and therefore remain implanted within the patient after use, which may lead to other complications such as infection or irritation of the surrounding tissue.

Another example of knot replacement technology is the use of a tortuous path, wherein the suture is disposed upon or within a device that contains a tortuous path, wherein friction between the suture and the device is utilized to retain the suture. A potential shortcoming of such devices is that since the suture is not physically retained within the device there is the potential for the suture to slip or loosen from the device. Additionally, many of these devices require a great amount of operator skill or time to dispose the suture therethrough, thereby adding to the complexity of a potentially already complex surgical procedure.

Therefore, for the above reasons, it would be desirable to provide improved devices, systems, and methods for securing at least one length of suture that has been used to suture tissue together to close an opening formed in the tissue such as a vascular puncture. It would be particularly beneficial if these improved devices provided some or all of the benefits while overcoming one or more of the disadvantages discussed above.

It is an object of the present invention to provide methods and devices that may be utilized in place of forming a knot in a suture to effect a closure of the suture.

It is a further object of the present invention to provide a knot replacement device that reduces surgical time by eliminating the need to form a knot during a surgical procedure.

It is yet another object of the present invention to provide a knot replacement device with is biocompatible and absorbable, thereby reducing the amount of foreign material remaining implanted within a patient after a surgical procedure.

These and other objects of the present invention will be apparent from the following detailed description and the claims.

SUMMARY OF THE INVENTION

The present invention provides methods and apparatuses that may be utilized to secure at least one end of a suture and retain the suture. The device according to the present invention includes an outer body and an inner wedge member, wherein the outer body includes an opening formed therein, the opening configured to receive at least one suture therethrough. The opening further being sized and configured to receive the inner wedge member therein, whereby the suture and the inner wedge member are frictionally retained within the opening.

In accordance with the present invention there is provided a suture lock device, the suture lock device including an outer body member having a lumen extending therethrough, the lumen defining a suture path through the outer body, an inner wedge member axially insertable into the outer body member to secure a portion of a suture between the wedge and the interior surface of the lock member, an outer tube having a proximal end and a distal end, the outer tube carrying the outer body member at the distal end of the outer tube, the outer tube carrying the wedge proximal to the outer body member, and a pusher member slidable within the outer tube to push the wedge into the lock member.

In accordance with the present invention there is provided a method of securing and trimming a suture, the method comprising: providing a suturing locking device comprising an outer body member having an aperture disposed therethrough, the aperture defining a suture path through the outer body member; a wedge axially insertable into the outer body member to secure a portion of a suture between the wedge and the interior surface of the outer body member; an outer tube having a proximal end and a distal end, the outer tube carrying the outer body member at the distal end of the outer tube, the outer tube carrying the wedge proximal to the outer body member the outer tube defining a suture tail opening; and a pusher member slidable within the outer tube to push the wedge into the outer body member; advancing a suture through the outer body member and through the suture tail opening; pushing the wedge member into the outer body member to secure the suture; and cutting the suture by shearing the suture between the outer body member and an edge of the suture tail opening.

BRIEF DESCRIPTION OF THE DRAWINGS

Referring now to the appended drawings, wherein like numerals are utilized to denote similar objects.

DETAILED DESCRIPTION

Before the present invention is described in such detail, it is to be understood that this invention is not limited to particular variations set forth herein as various changes or modifications may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

In accordance with the present invention there are provided methods and apparatuses for fixedly retaining at least one suture without having to tie a knot in the suture. The devices in accordance with the present invention include a suture lock device and a delivery device, wherein the delivery device is configured to retain and deliver the suture lock device over at least one suture. The delivery device may further include a suture cutting mechanism, whereby after delivery of the suture lock device the suture is severed. The suture lock device may be constructed of a biocompatible material such as plastics, composites, metals or preferable of a bio-absorbable material.

Figure 1:
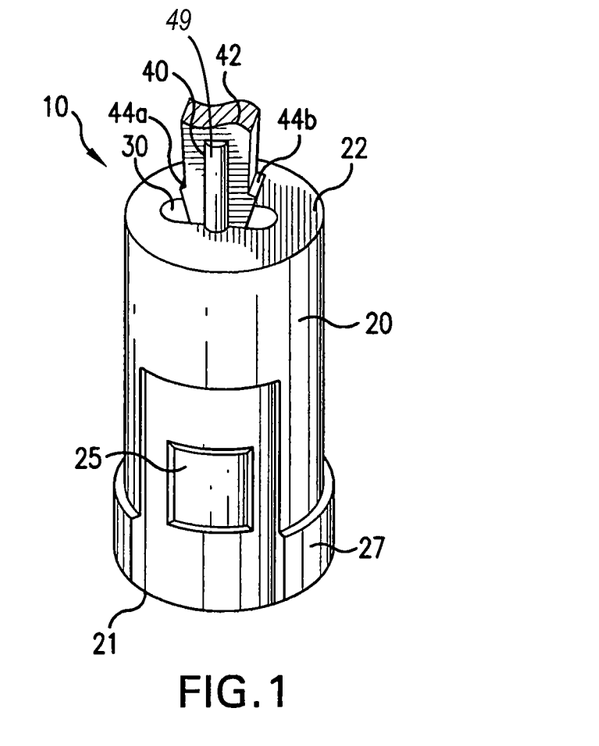
FIG. 1 is a perspective view of an exemplary embodiment of the suture lock in accordance with the present invention.

Referring now to FIG. 1 there is shown an exemplary embodiment of a suture lock device in accordance with the present invention. The suture lock device will be initially described herein, whereby the delivery device will be described in detail below. The suture lock device includes an outer body, the outer body including an aperture formed therethrough, and an inner wedge member. The inner wedge member is sized to be received within the aperture formed in the outer body.

As shown in FIG. 1, the suture lock 10 in accordance with the present invention comprises an outer body 20 having a proximal end 22 and a distal end 21. The outer body further includes an increased diameter section 27 disposed adjacent the distal end 21, wherein a recessed portion 25 extends from the distal end 21 and partially along the length of the body 20. The recessed portion 25 terminating a distance from the proximal end 22 of the body 20.

The outer body 20 further includes an aperture 30 disposed therethrough. The aperture 30 being sized and configured to receive an inner wedge member 40, wherein the inner wedge member includes at least one projection 44, and preferably two projections 44a and 44b disposed between the distal end 41 and the proximal end 42 of the inner wedge member 40.

The outer body 20 and the inner wedge member 40 will preferably be constructed of the same or similar materials. Examples of suitable materials for construction of the outer body 20 and the inner wedge 40 include plastics, composites, metals and ceramics. In a preferred embodiment the outer body and the wedge are constructed of a biocompatible material and more preferably of a biocompatible material that is also bio-absorbable. In a preferred embodiment, the outer body 20 is generally cylindrical in shape, though it is contemplated that the outer body 20 may be formed having other geometric shapes or configurations.

Figure 2:
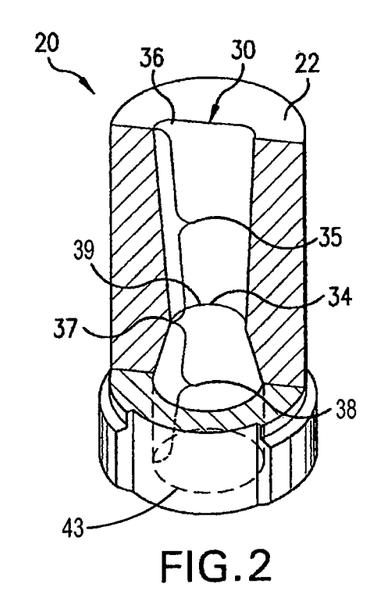
FIG. 2 is a partial cross-sectional view of the outer body of the suture lock of FIG. 1 as shown in the present invention.

Referring now to FIG. 2, there is shown a partial cross-sectional view of the outer body 20 in accordance with the present invention. As shown in FIG. 2, and as previously described, the outer body 20 includes an aperture 30 formed therethrough, wherein the aperture 30 is generally disposed along an axis extending through the outer body 20. The aperture 30 includes an upper portion 35 and a lower portion 40, wherein each of the portions are generally formed having a specific shape. As shown, the upper portion 35 is preferably formed in the shape of an inverted cone or funnel, wherein the opening has a larger diameter adjacent to its proximal end 36 and a smaller opening adjacent the distal end 37. As described above, the aperture 30 is constructed having two portions 35 and 40, wherein the lower portion 40 is preferably formed in the shape of a cone or funnel and has a larger opening adjacent its distal end 41 and a smaller opening adjacent its proximal end 42. As shown in FIG. 2, the upper portion 35 and the lower portion 40 of the aperture 30 are aligned along an axis generally extending through the center of the outer body 20, thereby forming the aperture 30 having a proximal end 32 and a distal end 33 such that the aperture 30 includes a reduced diameter portion 34 where the upper and lower portions intersect.

Figure 3:
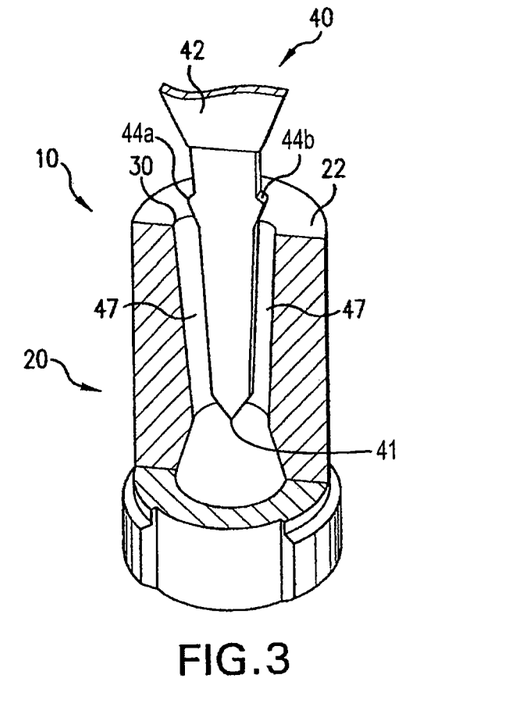
FIG. 3 is a cross-sectional view of the suture lock in accordance with the present invention.

Referring now to FIG. 3 there is shown a partial cross-sectional view of the suture lock 10 in accordance with the present invention, wherein the inner wedge member 40 is shown partially disposed within the aperture 30 formed in the outer body 20. As shown in FIG. 3, the inner wedge member 40 includes at least one projection and more preferably two projections 44a and 44b, wherein, as shown, the projection is sized such that it does not contact the wall of the aperture 30. Thus, when the inner wedge member 40 is disposed within the aperture 30, the projections 44 and the inner wedge member form a space 47 between the inner wedge member 40 and the aperture 30. The inner wedge member 40 may be configured to be fully received within the aperture 30 of the outer body 20 or be configured such that a portion of the inner wedge member adjacent the proximal end 42 extends beyond a proximal surface 22 of the outer body.

Figure 4:
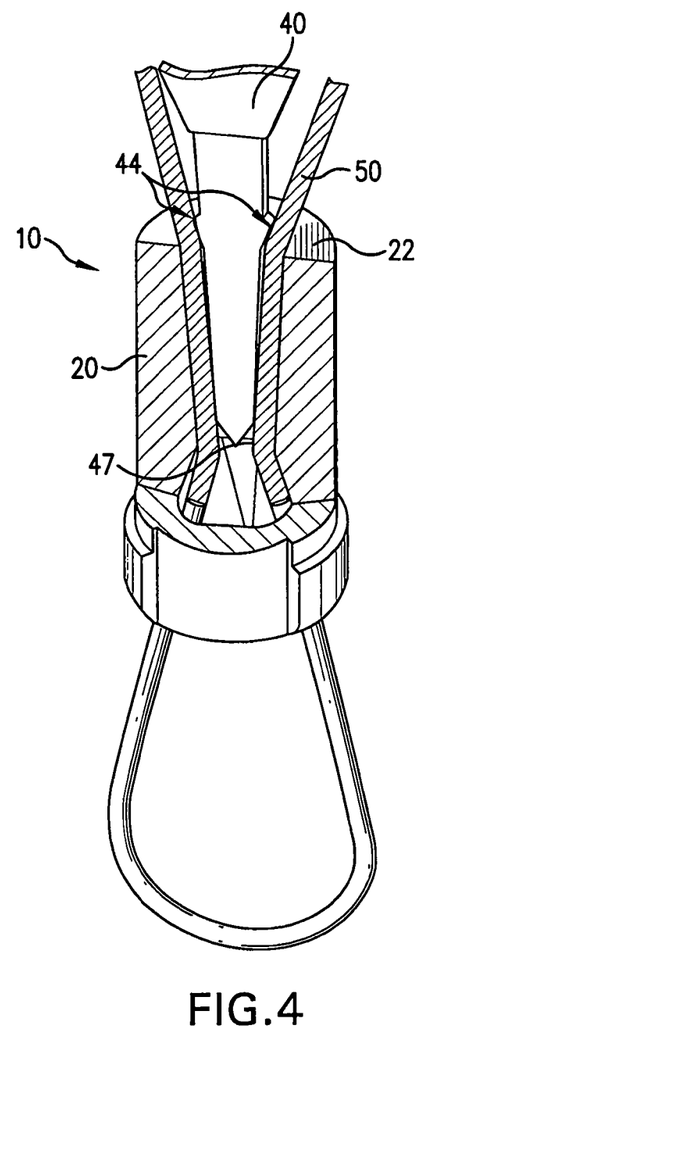
FIG. 4 is a cross-sectional view of the outer body wherein at least one suture has been disposed therein and the inner wedge member has been partially disposed within an opening formed in the outer body.

Referring now to FIG. 4 there is shown a cross-sectional view of the suture lock 10 in accordance with the present invention wherein a loop of suture 50 has been disposed through the space 47 formed between the aperture 30 of the outer body 20 and the inner wedge member 40. As shown in FIG. 4, the suture 50 is in communication with the wedge 40 and the wall of the aperture 30 and wherein projections 44 engage a surface of the suture 50. The space 47 is sized and dimensioned so that the frictional forces between the suture and the components described above provide a sufficient amount of force to retain the suture and the inner wedge member within the aperture 30. As shown in FIG. 4, the inner wedge member is not fully disposed within the aperture 30. In use, the inner wedge member 40 would be advanced into the aperture 30 of the outer body 20 until the projections 44a and 44b are sufficiently contained within the aperture 30 of the outer body. It is further contemplated that the inner wedge member may be configured to extend beyond the proximal end of the outer body member 20 when disposed in a final position.

Figure 5:
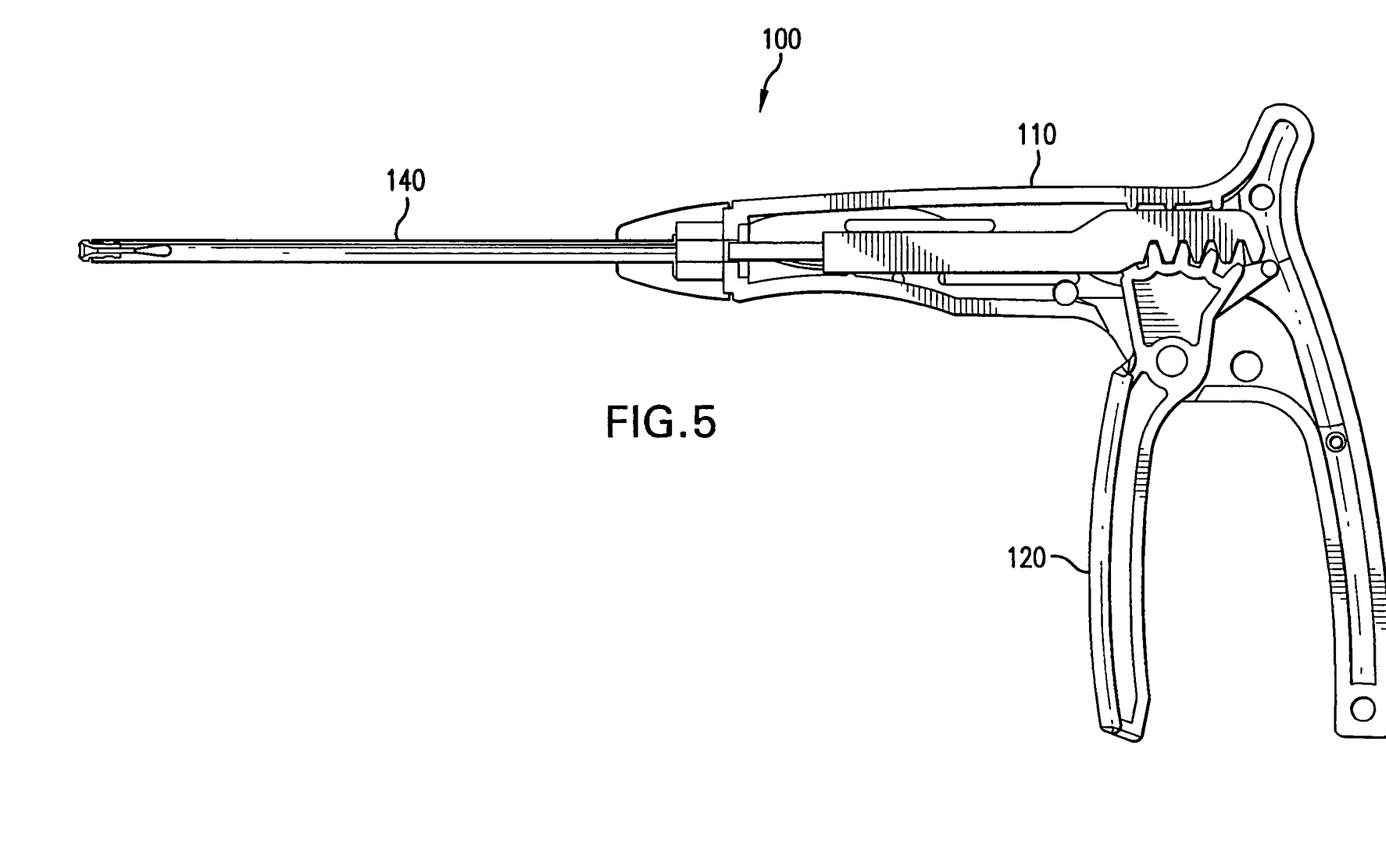
FIG. 5 is a plan view of a delivery device and the suture lock in accordance with the present invention.

Referring now to FIG. 5 of the present invention there is shown an exemplary embodiment of a delivery device in accordance with the present invention. The delivery device includes a handle member including a trigger and an elongated shaft portion, wherein the elongated shaft portion is configured to engage and deploy the suture lock in accordance with methods of the present invention.

As shown in FIG. 5, the delivery device 100 includes a handle member 110 having a trigger 120 and an elongate tube member 140 extending from a distal end of the handle member 110.

Figure 6:
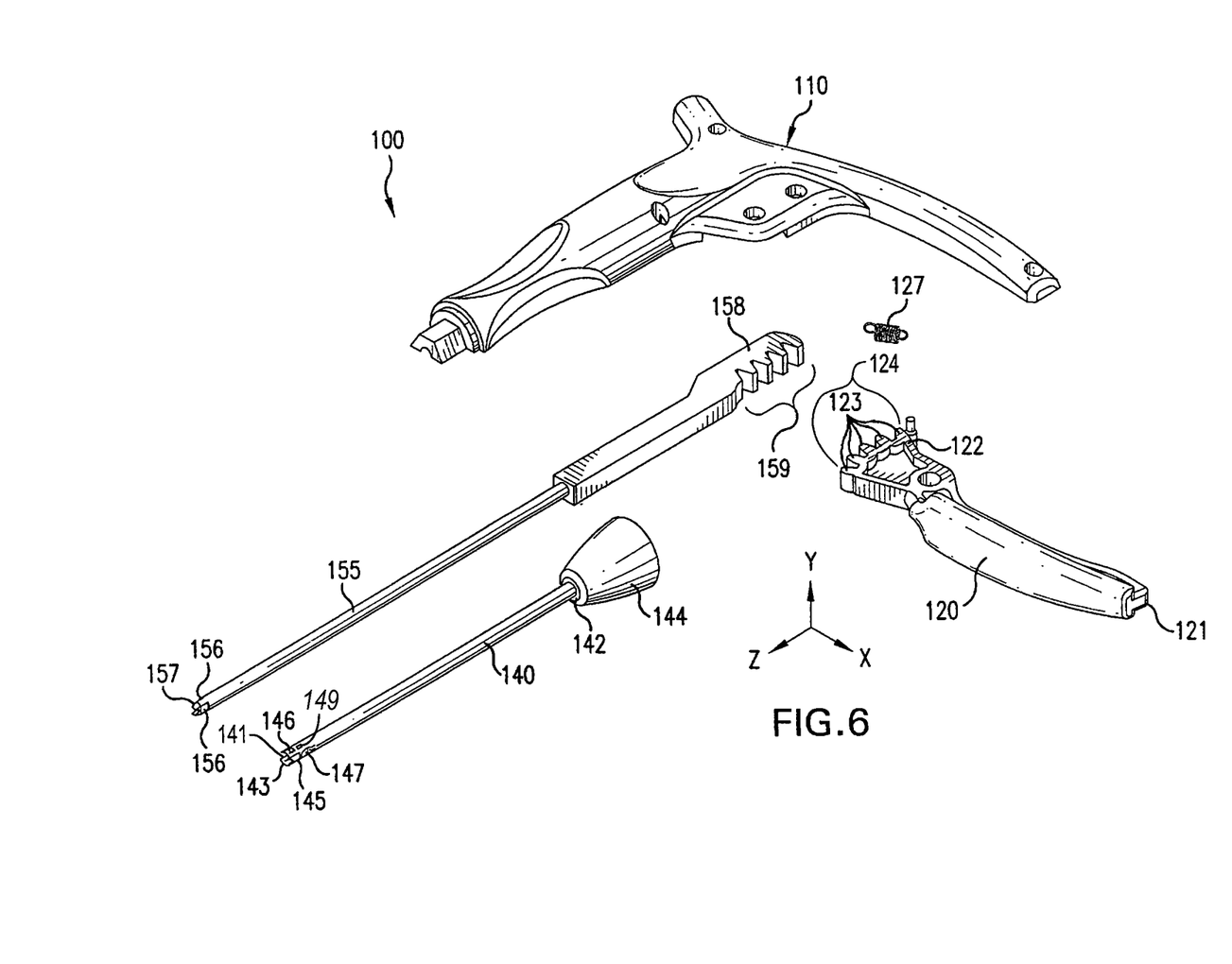
FIG. 6 is an exploded assembly view of the delivery device in accordance with the present invention.

Referring now to FIG. 6, there is shown an exploded view of the delivery device 100 in accordance with the present invention wherein only one side of the handle member 110 is shown. In accordance with the present invention, the delivery device includes a handle member 110 and an elongated tubular member 140. The handle member 110 is configured to house a trigger member 120 and a pusher member 155, wherein the trigger member 120 is configured to be in communication with a proximal portion of a pusher member 155. The pusher member being configured to be slidably disposed within the elongated tubular member 140.

Referring now to the trigger member, the trigger member 120 has a distal end 121 and a proximal end 122, wherein the proximal end includes a plurality of projections 123, whereby the plurality of projections form a gear member 124. The trigger member 120 further includes a biasing member 127, the biasing member is configured to be in communication with a portion of the trigger member 120 and the handle member 110.

Referring now to the pusher member, the pusher member 155 includes a distal end 157 and a proximal end 158, wherein the proximal end includes a plurality of projections formed therein, wherein the projections form a gear member 159. The gear member 159 of the pusher member 155 is configured to engage the gear member 124 of the trigger member. Wherein, movement of the trigger member 120 will be translated to the pusher member 155 through the interaction of the gear members. The distal end 157 of the pusher member 155 is configured to engage and detachably retain the inner wedge member 40. Further still, the pusher member 155 includes at least one cutting member 156 disposed adjacent the distal end 157 thereof, wherein the cutting member 156 will be further described below in connection with methods according to the present invention.

Referring now to the elongated tubular member 140, wherein the elongated tubular member 140 has a proximal end 142 and a distal end 143 with a bore 141 extending therebetween. The bore 141 is configured to slidably receive the pusher member 155 as described above. As shown in FIG. 6, a hub 144 may be disposed at or about the proximal end of the elongated tubular member 140, wherein the hub is configured to engage the two halves of the handle member 110 thereby retaining the two halves of the handle members. The distal end of the tubular member 140 will be described in greater detail below with reference to FIG. 7.

Figure 7:
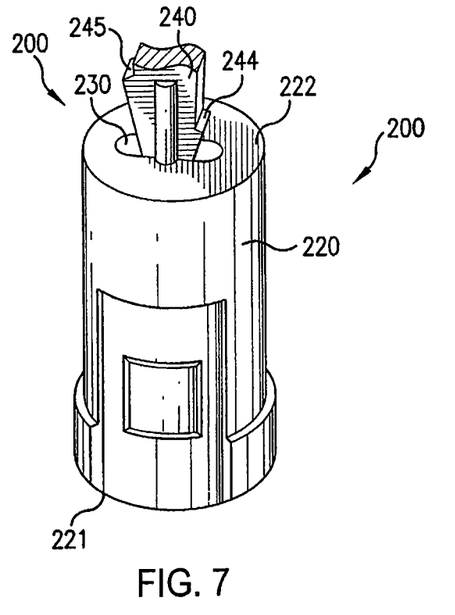
FIG. 7 is a plan view of an alternative embodiment of a suture lock in accordance with the present invention.

Referring now to FIG. 7, there is shown a partial view of the distal end 143 of the tubular member 140. The distal end 143 of the tubular member 140 further includes at least one tab 146 formed therein, whereby the tab is formed in the wall of the tubular member adjacent to the distal end, such that a portion of the tab may be configured to extend into the bore 141 of the tubular member 140. The tab 146 of the tubular body 140 is configured to engage the recessed portion 25 of the outer housing 20 as will be described in greater detail below with regard to the methods according to the present invention. The tubular member 140 further includes a suture tail opening 147 disposed adjacent to the distal end 143, wherein the suture tail opening 147 is configured and sized to receive a suture therethrough.

In addition to that described above, the tubular body 140 additionally includes at least one and more preferably two wedge retention tabs 149. The wedge retention tabs 149 are formed in the wall of the tubular body adjacent to the distal end 143 thereof. The wedge retention tabs are configured to detachably retain the inner wedge member in a position adjacent to the proximal end 22 of the outer body 20 and adjacent to the suture tail opening 147. The function of the wedge retaining tabs 149 will be described in more detail below with regard to the methods of use of the present invention.

Figure 8:
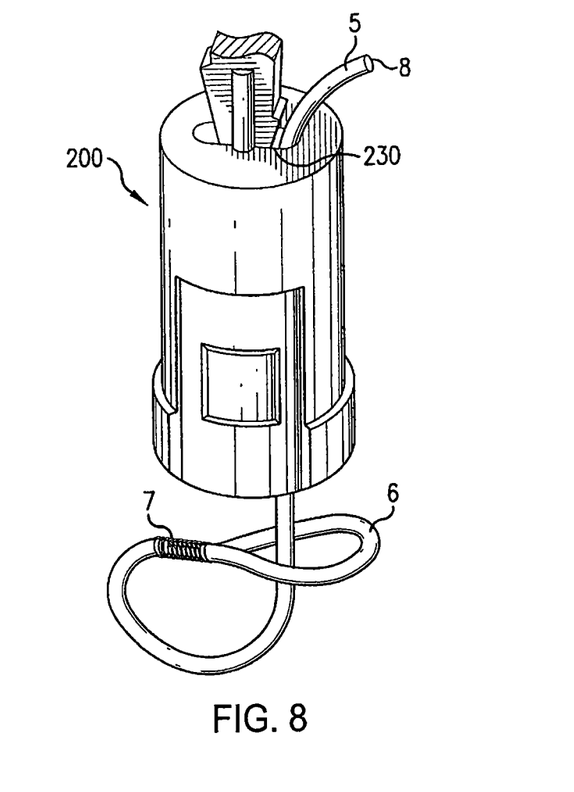
FIG. 8 is a cross-sectional view of the alternative embodiment of the suture lock in accordance with the present invention.

Referring now to FIG. 8, there is shown an exemplary embodiment of an alternative embodiment of a suture lock in accordance with the present invention, wherein like numerals have been utilized to denote similar components.

As shown in FIG. 8, the suture lock 200 in accordance with the alternative embodiment includes an outer body 220 having a proximal end 222 and a distal end 221 and an aperture 230 formed therethrough. The suture lock 200 further includes an inner wedge member 240, wherein the inner wedge member is sized and configured to be received within the aperture 230 of the outer body 220. As shown in FIG. 8, the inner wedge member includes a projection 244 formed on one side thereof and an alignment member 245 disposed on the other side thereof. Suture lock 200 is configured to be used in conjunction with a single suture tail as will be described below with reference to FIG. 9.

Figure 9:
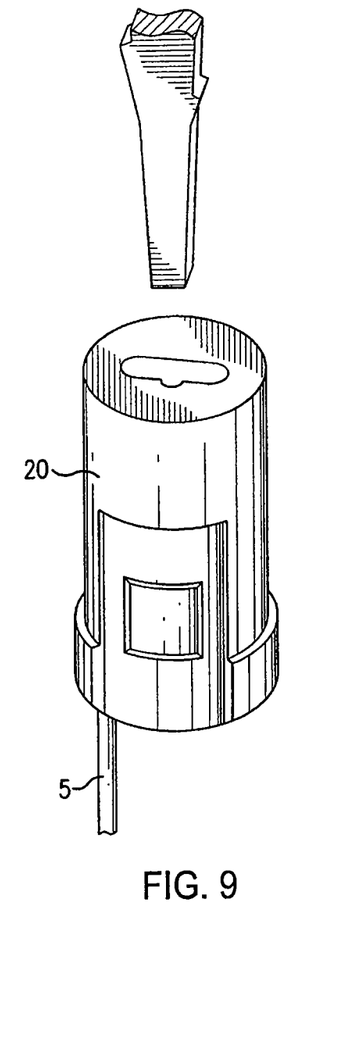
FIG. 9 is another exemplary embodiment of another alternative embodiment of a suture lock in accordance with the present invention.

Referring now to FIG. 9, there is shown the suture lock 200 in accordance with the present invention wherein a suture 5 has been disposed through the aperture 230 of the suture lock 200. As shown in FIG. 9, the suture 5 is configured such that the suture only includes a single suture tail, wherein the suture includes a pre-formed loop 6 formed therein. The pre-formed loop may be formed by tying a knot in the suture using known knot tying methods, or the loop may be formed in the suture during manufacture of the suture. For example, the loop may be formed using molding, extrusion or heat forming. As shown in FIG. 9, the suture tail 8 is passed through the loop 6 and then passed through the aperture 230 of the suture lock, wherein the inner wedge member 240 is disposed within the lumen, such that the suture is frictionally retained between the wall of the aperture and the inner wedge member. It is contemplated that the suture loop may be formed with a sliding knot 7, wherein the sliding knot allows the loop to close down on the suture passed through the loop, thereby locking the suture and the loop together.

Figure 10:
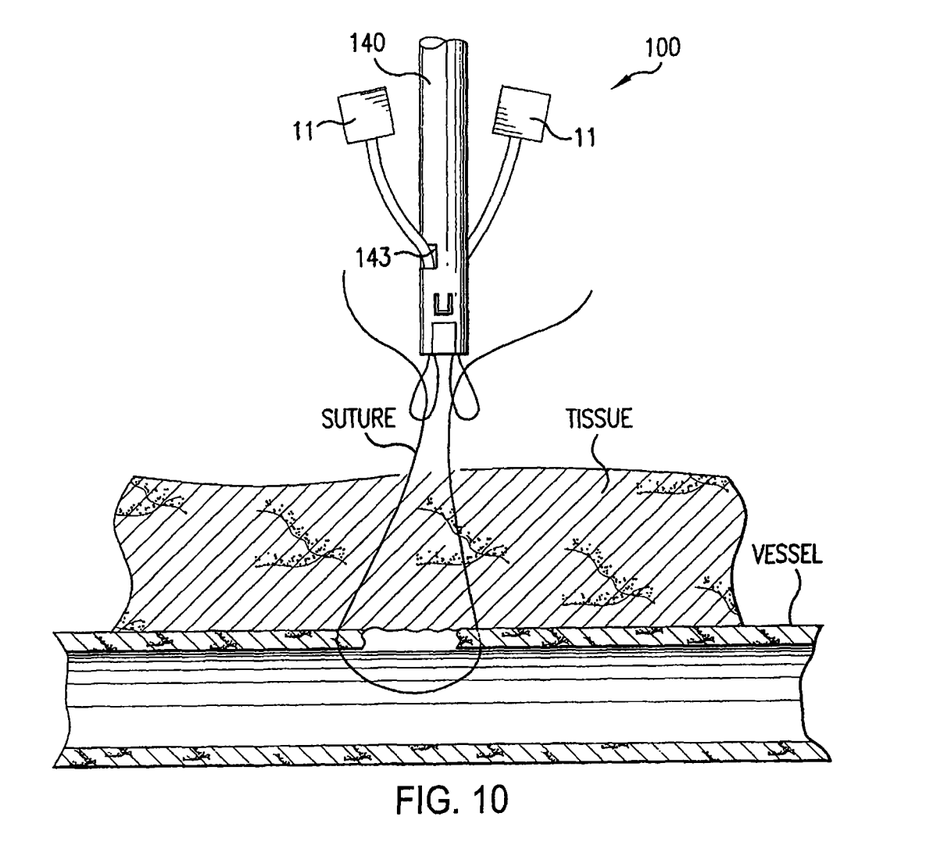
FIG. 10 is a perspective view of a vessel having an opening formed therein and illustrating the use of the delivery device of the present invention with the suture lock disposed therein.

In yet another alternative embodiment as shown in FIG. 10, it is contemplated that one end of the suture 5 may be overmolded with the outer body 20 as shown, thereby eliminating the need for a suture loop as previously described. By overmolding one end of the suture within the outer body of the suture lock, one end of the suture is fixedly retained within the outer housing body, thereby eliminating the need for a pre-formed suture loop. Further still, in use, the other end of the suture does not need to be passed through a pre-formed loop before being disposed through the patient's tissue adjacent the opening to be closed, thereby simplifying the closure process.

Methods of Use

The device according to the present invention will now be described in use, the description of the methods below should be considered exemplary in nature and should not be considered limiting in any manner.

Figure 11:
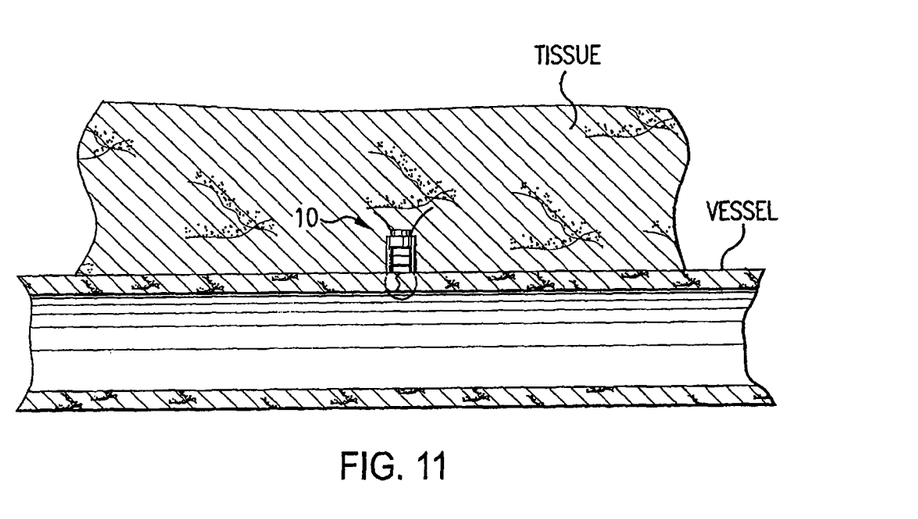
FIG. 11 is a plan view of the vessel after deployment of the suture lock device in accordance with the present invention to effect vessel closure.

Referring now to FIG. 11, there is shown a cross-sectional view of a patient's vessel, wherein a suture has been placed across the opening in the vessel wall using a device such as that disclosed in U.S. Pat. No. 6,136,010, the entirety of which is herein incorporated by reference. After placing the suture across the opening, the ends of the suture are drawn through the outer body 20 of the suture lock 10 with the use of a suture snare 11 as shown in FIG. 11, thereby passing the suture ends through the aperture 30 of the outer body and wherein the ends of the suture extend through the suture tail openings 147 formed in the elongated tubular member 140.

After the suture ends have been disposed through the suture lock 10 and the elongated tubular member, the operator utilizes the handle of the delivery device 100 to place the distal end of the suture lock adjacent to the opening formed in the vessel as shown in FIG. 12. In addition to placing the distal end of the suture lock adjacent to the vessel surface, the user applies tension to the suture ends. Once the suture lock 10 is placed in a desired position, and sufficient tension is applied to the suture ends, the operator then actuates the trigger 120 of the delivery device.

Upon actuation of the trigger 120, the pusher member engages the inner wedge member 40 and advances the inner wedge member 40 into the aperture 30 of the outer body 20, wherein the inner wedge member is released from the wedge retention tabs 149 by the pusher member 155. The pusher member 155 drives the inner wedge member 40 into the aperture 30. The projections 44a and 44b engage the suture wherein the suture frictionally engages the inner wall member of the aperture 30 adjacent to the inner wedge member 40. Once the inner wedge 40 has been disposed within the aperture 30, the pusher member 155 continues to advance thereby applying a force to the inner wedge member, such that the force applied to the inner wedge member is greater than the retention force applied by the tabs 146 to the outer body member 20, thereby expelling the suture lock from the distal end of the delivery device 100. Additionally, the suture ends which have been disposed through the suture tail openings 143 are severed by the distal movement of the pusher member 155.

Once the suture lock 10 has been expelled from the delivery device 10, the delivery device can then be removed from the tissue tract of the patient. The suture and the suture lock 10 remain within the vessel and adjacent to the vessel to close the opening formed in the vessel wall.

It is contemplated that the delivery device 10 may include a lumen extending from the handle to the distal end of the device, wherein the lumen may be configured to deliver a beneficial agent adjacent to the opening in the vessel wall, or at any location within the tissue tract. It is further contemplated that the suture lock in accordance with the present invention may be deployed through a sheath or other medical device which may be deployed within the tissue tract.

Although the present invention has been described for use with a suture having two suture ends it is contemplated according to the alternative embodiments of the present invention that the suture lock may be integrally formed with one end of the suture or be used with a suture having a pre-formed loop, wherein the free suture end would be passed through the suture loop, through the vessel wall, across the opening and back through the tissue wall, whereby the free end of the suture would then be passed through the aperture of the suture lock. It is further contemplated that the suture lock may be integrally formed with a suture delivery device such as that shown and described in U.S. Pat. No. 6,136,010, wherein the device of the '010 patent would deliver a suture across an opening and deploy the suture lock to close the opening in the tissue.

Although the present invention has been shown and described as being utilized to close an opening formed in a vessel wall, it is contemplated that the suture lock may be utilized to close other openings in tissue, such as PFOs.

It is further contemplated that the suture and the suture lock in accordance with the present invention may be constructed of a bio-absorbable material, thus, at a time after the surgical procedure no foreign material would remain within the patient's body.

Although the present invention has been described in connection with the preferred form of the device and methods of practicing it and modifications thereto, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

What is claimed is:

1. A suturing securing device comprising:
   an outer body member having a proximal end, a distal end, and a lumen extending therethrough, the lumen defining a suture path through the outer body, a longitudinal recessed portion extending from the distal end and around a portion of the outer body member less than an entire circumference of the outer body member, a distal-most end having an increased diameter section extending radially outward from an outer surface of the outer body member, the increased diameter section extending around less than an entire circumference of the distal end;
   a wedge axially insertable into the outer body member to secure a portion of a suture between the wedge and an interior surface of the outer body member;
   an outer tube having a proximal end and a distal end, the outer tube carrying the outer body member at the distal end of the outer tube, the outer tube carrying the wedge proximal to the outer body member; and
   a pusher member slidable within the outer tube to push the wedge into the outer body member.

2. The suture securing device of claim 1, wherein the outer tube defines at least one suture tail opening proximal to the distal end of the outer tube.

3. The suture securing device of claim 2, wherein the pusher member has a suture cutter positioned to slide past the suture tail opening of the outer tube such that a suture tail extending through the suture tail opening will be cut upon the pusher member being moved distally with respect to the outer tube.

4. The suture securing device of claim 3, wherein the pusher member pushes the outer body member out the distal end of the outer tube after pushing the wedge into the outer body member.

5. The suture securing device of claim 2, wherein the outer body member defines a distally facing ledge, wherein the outer tube defines a proximally facing tab positioned distal to the distally facing ledge when the outer body member is carried within the outer tube, the tab being bent inward to cooperate with the distally facing ledge to detachably retain the outer body member in the outer tube.

6. The suture securing device of claim 5, wherein the pusher member pushes the wedge and outer body member with sufficient force to move the outer body member past the proximally facing tab to eject the outer body member from the outer tube.

7. The suture securing device of claim 1, wherein the wedge further includes at least one projection formed thereon, said projection disposed adjacent a proximal end of the wedge.

8. The suture securing device of claim 1, wherein the wedge further includes a key member that aligns with a key slot located on an inner surface of the outer body member.

9. The suture securing device of claim 1, wherein the lumen has an elliptical-shaped opening and an elliptical cross section throughout a proximal portion.

10. A suturing securing device comprising:
    an outer body member having a proximal end, a distal end, and a lumen extending therethrough, the lumen defining a suture path through the outer body member, with a portion of the distal end having a larger diameter than the proximal end and a longitudinal recessed portion extending from the distal end and around a portion of the outer body member less than an entire circumference of the outer body member;
    a wedge axially insertable into the outer body member to secure a portion of a suture between the wedge and an interior surface of the outer body member;
    an outer tube having a proximal end and a distal end, the outer tube carrying the outer body member at the distal end of the outer tube, the outer tube carrying the wedge proximal to the outer body member; and
    a pusher member slidable within the outer tube to push the wedge into the outer body member.

11. The suture securing device of claim 10, wherein the distal end of the outer body member has another portion with a diameter smaller than the proximal end of the outer body member.

12. The suture securing device of claim 10, wherein the outer body member defines a distally facing ledge, wherein the outer tube defines a proximally facing tab positioned distal to the distally facing ledge when the outer body member is carried within the outer tube, the tab being bent inward to cooperate with the distally facing ledge to detachably retain the outer body member in the outer tube.

13. A method of securing and trimming a suture, the method comprising:
    providing a suturing locking device comprising:
       an outer body member having a proximal end, a distal end, and an aperture disposed therethrough, the aperture defining a suture path through the outer body member, at least one recessed portion extending from the distal end and partially along a longitudinal length of an outer surface of the outer body member;

a wedge axially insertable into the outer body member to secure a portion of a suture between the wedge and an interior surface of the outer body member;

an outer tube having a proximal end and a distal end, the outer tube carrying the outer body member at the distal end of the outer tube, the outer tube carrying the wedge proximal to the outer body member, the outer tube defining a suture tail opening; and a pusher member slidable within the outer tube to push the wedge into the outer body member;

wherein the outer body member includes wedge retention tabs that detachably retain the wedge in a position adjacent to the proximal end of the outer body member, the pusher member pushing the wedge so as to release the retention tabs and push the wedge into the outer body member;

advancing a suture through the outer body member and through the suture tail opening;

pushing the wedge into the outer body member to secure the suture; and cutting the suture by shearing the suture between the outer body member and an edge of the suture tail opening.

14. The method according to claim 13, wherein the wedge retention tabs detachably retain the wedge in alignment with the recessed portion of the outer body member.

15. The method according to claim 13, wherein the step of advancing a suture through the outer body member includes using a suture snare to dispose the suture through the outer body member and through the suture tail opening.

16. The method according to claim 13, wherein the wedge further includes a projection, the projection configured to frictionally engage the suture when the wedge is disposed within the aperture.

* * * * *